(12) United States Patent

Bartholomäus et al.

(10) Patent No.: US 7,611,730 B2
(45) Date of Patent: *Nov. 3, 2009

(54) TRAMADOL-BASED MEDICAMENT

(75) Inventors: Johannes Bartholomäus, Aachen (DE); Elmar Josef Friderichs, Stolberg (DE)

(73) Assignee: Grunenthal GmbH, Aachen (DE)

( * ) Notice: Subject to any disclaimer, the term of this patent is extended or adjusted under 35 U.S.C. 154(b) by 906 days.

This patent is subject to a terminal disclaimer.

(21) Appl. No.: 10/641,779

(22) Filed: Aug. 15, 2003

(65) Prior Publication Data

US 2004/0076669 A1 Apr. 22, 2004

Related U.S. Application Data

(63) Continuation of application No. PCT/EP02/01763, filed on Feb. 20, 2002.

(30) Foreign Application Priority Data

Feb. 21, 2001 (DE) .................. 101 08 122

(51) Int. Cl.
 *A61K 9/22* (2006.01)
 *A61K 31/205* (2006.01)
 *A61K 31/135* (2006.01)
(52) U.S. Cl. .................. 424/468; 514/554; 514/650
(58) Field of Classification Search ............... 424/468; 514/554, 650
See application file for complete search history.

(56) References Cited

U.S. PATENT DOCUMENTS 6,436,438 B1 * 8/2002 Momberger et al. ........ 424/458

6,576,260 B2 * 6/2003 Bartholomaeus et al. .... 424/469
6,599,529 B1 * 7/2003 Skinhøj et al. .............. 424/458
2005/0238715 A1 * 10/2005 Liu et al. .................... 424/468

FOREIGN PATENT DOCUMENTS

| DE | 19601744 A1 | 7/1997 |
|----|----|----|
| DE | 19630035 A1 | 1/1998 |
| DE | 9422335 U1 | 5/2000 |
| DE | 19927689 A1 | 12/2000 |
| EP | 0642788 A2 | 3/1995 |
| EP | 0787715 B1 | 8/1997 |
| EP | 1005861 A1 | 6/2000 |
| GB | 2317110 A | 3/1998 |
| WO | WO 98/40053 | 9/1998 |
| WO | WO 99/42095 | 8/1999 |
| WO | WO 00/32558 | 6/2000 |

OTHER PUBLICATIONS

"Complementary And Synergistic Antinociceptive Interaction Between The Enantiomers Of Tramadol", Raffa et al., Journal of Pharmacology and Experimental Therapeutics, 1993, 267(1), 331-40.
"Analgesic Efficacy And Safety Of Tramadol Enantiomers In Comparison With The Racemate: A Randomised, Double-Blind Study With Gynaecological Patients Using Intravenous Patient-Controlled Analgesia", Ground et al., Pain, Elsevier Science Publishers, vol. 62, No. 3, 1995.
"Tramadol Induces Antidepressant-Type Effects In Mice", Rojas-Corrales et al., Life Sciences, vol. 63, No. 12, 1998.
Arzneim.-Forschung. Drug Res. 28, 1978, pp. 114-121.

* cited by examiner

*Primary Examiner*—Jennifer M Kim
(74) *Attorney, Agent, or Firm*—Norris McLaughlin & Marcus PA

(57) ABSTRACT

The invention relates to a medicament containing the racemate of tramadol in a retarded form and the (+)-enantiomer of tramadol in a non-retarded form.

53 Claims, No Drawings

TRAMADOL-BASED MEDICAMENT

This application is a continuation of international application number PCT/EP02/01763 filed Feb. 20, 2002, status pending.

The present invention relates to a medicament containing the racemate of tramadol in slow-release form and the (+)enantiomer of tramadol in immediate-release form.

The active pharmaceutical ingredient tramadol is normally employed in the form of its racemate composed of (+)-tramadol—i.e. (1R,2R)-2-[(dimethylamino)-methyl]-1-(3-methoxyphenyl)cyclohexanol and (−)-tramadol—i.e. (1S,2S)-2-[(dimethylamino)methyl]-1-(3-methoxyphenyl)cyclohexanol—for controlling moderately severe to severe pain. However, when a certain intensity of pain is exceeded, the analgesic efficacy of tramadol is frequently no longer sufficient for satisfactory therapy of the patient's pain.

The analgesic efficacy of tramadol results from a complicated interplay of its enantiomers by a mechanism which comprises a non-opioid in addition to an opioid component of action. The opioid component of action, which makes an essential contribution to the analgesic efficacy of tramadol, is attributable to the (+)enantiomer of tramadol and the corresponding metabolite, (+)-O-demethyltramadol.

Thus a metabolic activation of (+)-tramadol and that of (−)-tramadol is brought about by the enzyme CYP2D6, the availability of which in the patient's body is not unlimited. An improvement in the analgesic efficacy of tramadol above a certain pain limit or immediately after administration to the patient therefore cannot be achieved sufficiently by an increase in the dosage of racemic tramadol.

One object of the present invention was therefore to provide a tramadol-based medicament which is also suitable for complete suppression or at least marked alleviation of very severe pain, especially in the initial phase of pain control.

This object is achieved according to the invention by providing a medicament which contains the racemate of tramadol in slow-release form and the (+)enantiomer of tramadol in immediate-release form.

The preparation and, where appropriate, the purification and/or isolation of (+)-tramadol can take place by conventional methods known to the skilled worker, described, for example, in Frankus et al., Arzneim.-Forschung. Drug Res. 28, pages 114-121, 1978 or in EP 0 787715 B1. The corresponding documents are hereby incorporated by reference and are thus regarded as part of the disclosure. The racemate of tramadol is generally available on the market.

The medicament of the invention may also contain at least one of the active ingredient components, the racemate or the (+)enantiomer of tramadol, in the form of at least one corresponding physiologically tolerated salt.

These physiologically tolerated salts are preferably selected from the group of chloride, bromide, sulfate, sulfonate, phosphate, tartrate, teoclate, embonate, formate, acetate, propionate, benzoate, oxalate, succinate, citrate, diclofenacate, naproxenate, salicylate, acetylsalicylate, glutamate, fumarate, aspartate, glutarate, stearate, butyrate, malonate, lactate, mesylate, saccharinate, cyclamate and acesulfamate, particularly preferably from the group of chloride, sulfate, saccharinate, teoclate, embonate, diclofenacate, naproxenate and salicylate. The salt of the respective active ingredient component which is very particularly preferred is the corresponding chloride.

The physiologically tolerated salts or acid addition salts can be obtained by the conventional methods known to the skilled worker, for example by reacting tramadol racemate or (+)-tramadol with the appropriate acid, preferably in aqueous solution.

The medicament of the invention preferably contains from 10 to 75% by weight of (+)-tramadol and from 90 to 25% by weight of slow-release racemic tramadol, particularly preferably from 20 to 50% by weight of (+)-tramadol and from 80 to 50% by weight of the slow-release racemic tramadol, where these amounts are each calculated as active ingredient and not as active ingredient salt and are based on the total amount of active ingredients.

The medicament of the invention is suitable preferably for parenteral or oral, particularly preferably for oral, administration. Medicaments which can be administered orally mean in this connection according to the invention those medicaments which are absorbed in the mouth region and those which are taken by mouth but are absorbed only in the gastrointestinal tract.

In a preferred formulation form, the medicament of the invention is in the form of syrups, transmucosal therapeutic systems, transdermal therapeutic systems, suspensions, tablets, multilayer tablets, coated tablets, capsules, suppositories, easily reconstituted dry preparations or powders. In a particularly preferred embodiment, the medicament of the invention is in the form of tablets, multilayer tablets, capsules or as suspension.

In a particularly preferred embodiment, the slow-release tramadol racemate and the (+)enantiomer of tramadol in the medicament of the invention are each in subunits formulated separately from one another.

Subunits for the purposes of the present invention are solid formulations which, besides the respective active ingredient component, may also comprise physiologically tolerated excipients.

The subunits of the medicament of the invention are preferably in multiparticulate form. Preferred multiparticulate subunits are microtablets, microcapsules, granules, active ingredient crystals or pellets. The multiparticulate subunits are particularly preferably in the form of microtablets, granules or pellets.

The multiparticulate forms can be formulated to give a medicament of the invention by conventional methods known to the skilled worker, for example by packing into capsules or sachets, compression to tablets or by suspending in hydrophilic or lipophilic fluid. Where the medicament of the invention is in the form of a multilayer tablet, the subunits may be different layers of a multilayer tablet, preferably the layers of a bilayer tablet, or the multiparticulate subunits can be compressed to give such layers.

In a further preferred embodiment of the present invention, the medicament of the invention may comprise the slow-release tramadol racemate formulated in subunits which are provided inter alia with a coating containing (+)-tramadol.

Besides the active ingredient-containing coating and, where appropriate, slow-release coating of the racemate, the subunits may, where appropriate, also have at least one other coating which does not slow release and is applied directly as protective layer on the surface of the subunits.

Where the multiparticulate subunits are granules or pellets, these preferably have a size in the range from 0.1 to 3 mm, particularly preferably in the range from 0.5 to 2 mm. If the multiparticulate subunits are in the form of microtablets, these preferably have a diameter of from 0.5 to 5 mm, particularly preferably 1 to 3 mm and very particularly preferably from 1 to 2 mm.

If the multiparticulate subunits are active ingredient crystals or microcapsules, these preferably have a diameter of from 10 µm to 1 mm, particularly preferably from 15 µm to 0.5 mm. The diameter is very particularly preferably from 30 µm to 200 µm.

The medicament of the invention may additionally comprise, depending on the embodiment, as further ingredients, the usual physiologically tolerated excipients known to the skilled worker.

Where the medicament of the invention is in the form of tablets or microtablets, these may comprise as further physiologically tolerated excipients preferably microcrystalline cellulose, cellulose ethers, lactose, starch, starch derivatives, sugar alcohols and/or calcium hydrogen phosphate, and other conventional binders, flow regulators and/or lubricants and, where appropriate, disintegrants known to the skilled worker.

If the medicament of the invention is in the form of pellets or granules, they may comprise as further physiologically tolerated excipients preferably microcrystalline cellulose, cellulose ethers, lactose, starch, starch derivatives, sugar alcohols, calcium hydrogen phosphate, fatty alcohols, esters of glycerol and/or fatty acid esters.

If a medicament of the invention is in the form of microcapsules, these may comprise, depending on the nature of the method employed to produce them, the conventional physiologically tolerated excipients known to the skilled worker.

If the medicament of the invention is in the form of a suspension, this may, besides the physiologically tolerated suspending medium, comprise other conventional physiologically tolerated excipients known to the skilled worker, such as, for example, pH regulators, regulators to adjust the osmolality, surface-active compounds, viscosity regulators, buffers and/or preservatives.

The various formulation forms of the medicament of the invention can be produced by various methods known to the skilled worker.

Where the medicament of the invention is in the form of tablets, these can be produced for example by compressing the granules of the enantiomer which have been produced by wet, dry or melt granulation, and the granules of the racemate which have been produced correspondingly and whose release has been slowed in a suitable form, where appropriate with other physiologically tolerated excipients. The tablets can also be produced by compressing multiparticulate, optionally coated, pellets, active ingredient crystals or microcapsules, with slowing of release of the racemic components.

The formulations in the form of pellets can preferably be produced by extrusion and spheronization, by agglomerating pelletization or by direct pelletization in a high-speed mixer or in a rotary fluidized bed with simultaneous or subsequent slowing of release of the racemic component. The pellets are particularly preferably produced by extrusion of moist compositions and subsequent spheronization. The enantiomeric component is preferably applied in the form of a coating on the pellets.

Microcapsules are produced by conventional microencapsulation methods, such as, for example, by spray drying, spray congealing or coacervation, with a desired slowing of release of the racemic component.

In a preferred embodiment of the medicament of the invention, the slowing of release of the racemic tramadol is based on a release-slowing coating, on embedding in a release-slowing matrix, on attachment to an ion-exchange resin or a combination of at least two of the aforementioned release-slowing methods.

The release-slowing coating is preferably based on a water-insoluble, optionally modified natural or synthetic polymer or on a natural, semisynthetic or synthetic wax or fat or fatty alcohol or a mixture of at least two of these aforementioned components.

Water-insoluble polymers employed for producing a release-slowing coating are preferably poly(meth)acrylates, particularly preferably poly($C_{1-4}$)-alkyl (meth)acrylates, poly($C_{1-4}$)dialkylamino-($C_{1-4}$)-alkyl (meth)acrylates and/or copolymers thereof, very particularly preferably ethyl acrylate/methyl methacrylate copolymers with a monomer molar ratio of 2:1, ethyl acrylate/methyl methacrylate/trimethylammoniumethyl methacrylate chloride copolymers with a monomer molar ratio of 1:2:0.1, ethyl acrylate/methyl methacrylate/trimethylammoniumethyl methacrylate chloride copolymers with a monomer molar ratio of 1:2:0.2 or a mixture of at least two of the aforementioned polymers as coating material.

These coating materials are available on the market as 30% by weight aqueous latex dispersions under the name Eudragit RS30D®, Eudragit NE30D® and Eudragit RL30D®, respectively, and are also preferably employed as such as coating material.

It is likewise possible and preferred to employ polyvinyl acetates, where appropriate in combination with further excipients, as water-insoluble polymers for producing the release-slowing coating in the medicament of the invention. These are available on the market as aqueous dispersions containing 27% by weight polyvinyl acetate, 2.5% by weight povidon and 0.3% by weight sodium lauryl sulfate (Kollicoat SR 30 D®).

In a further preferred embodiment, the release-slowing coatings of the racemic tramadol are based on water-insoluble cellulose derivatives, preferably alkyl celluloses such as, for example, ethylcellulose, or of cellulose esters such as, for example, cellulose acetate as coating material. The coatings of ethylcellulose or cellulose acetate are preferably applied from aqueous pseudolatex dispersion. Aqueous ethylcellulose pseudolatex dispersions are marketed as 30% by weight dispersions (Aquacoat®) or as 25% by weight dispersions (Surelease®) and are preferably also employed as such as coating material.

Natural, semisynthetic or synthetic waxes, fats or fatty alcohols on which the release-slowing coating of the racemic tramadol can be based are preferably carnauba wax, beeswax, glycerol monostearate, glycerol monobehenate (Compritol ATO888®), glycerol ditripalmitostearate (Precirol ATO5®), microcrystalline wax, cetyl alcohol, cetylstearyl alcohol or a mixture of at least two of these components.

Whether the release-slowing coating is based on water-insoluble, optionally modified natural and/or synthetic polymers, the coating dispersion or solution may, besides the appropriate polymer, include a conventional, physiologically tolerated plasticizer known to the skilled worker in order to reduce the necessary minimum film-forming temperature.

Examples of suitable plasticizers are lipophilic diesters of aliphatic or aromatic dicarboxylic acid with $C_6$-$C_{40}$ and an aliphatic alcohol with $C_1$-$C_8$, such as, for example, dibutyl phthalate, diethyl phthalate, dibutyl sebacate or diethyl sebacate, hydrophilic or lipophilic esters of citric acid, such as, for example, triethyl citrate, tributyl citrate, acetyl tributyl citrate or acetyl triethyl citrate, polyalkylene glycols such as, for example, polyethylene glycols or propylene glycols, esters of glycerol such as, for example, triacetin, Myvacet® (acetylated mono- and diglycerides, $C_{23}H_{44}O_5$ to $C_{25}H_{47}O_7$), medium chain-length triglyceride (Miglyol®), with oleic acid or mixtures of at least two of the aforementioned plasticizers. Aqueous dispersions of Eudragit RS® and, where appropriate, Eudragit RL® preferably contain triethyl citrate as plasticizer.

The release-slowing coating preferably contains the plasticizer(s) in amounts of from 5 to 50% by weight, particularly preferably 10 to 40% by weight and very particularly preferably 10 to 30% by weight, based on the amount of the polymer employed. In individual cases, for example for cellulose acetate, larger amounts of plasticizers may also be employed, preferably up to 110% by weight.

It is additionally possible for the release-slowing coating to include other conventional excipients known to the skilled worker, such as, for example, lubricants, preferably talc or glycerol monostearate, colored pigments, preferably iron oxides or titanium dioxide, or surfactants such as, for example, Tween 80®.

The profile of release of the slow-release tramadol racemate in the medicament of the invention can be adjusted by conventional methods known to the skilled worker, such as, for example, for the thickness of the coating or for the use of further excipients as ingredients of the coating. Examples of suitable excipients are hydrophilic or pH-dependent pore formers such as, for example sodium carboxymethylcellulose, cellulose acetate phthalate, hydroxypropylmethylcellulolse acetate succinate, lactose, polyethylene glycol or mannitol or water-soluble polymers such as, for example, polyvinylpyrrolidone or water-soluble celluloses, preferably hydroxypropylmethylcellulose or hydroxypropylcellulose.

The release-slowing coating may also comprise insoluble or lipophilic excipients such as, for example, alkylized silicon dioxide, which is marketed for example as Aerosil R972®, or magnesium stearate, to enhance the slowing of release further.

The medicament of the invention itself may also have at least one coating which does not slow release. This may be, for example, a coating to improve the taste or a coating which is resistant to gastric fluid and shows pH-dependent dissolution. The coating which is resistant to gastric fluid allows the corresponding formulation of the medicament of the invention to pass through the gastric tract undissolved, and active ingredient components to be released only in the intestinal tract. The coating which is resistant to gastric fluid preferably dissolves at a pH of between 5 and 7.5.

The coating which is resistant to gastric fluid is preferably based on methacrylic acid/methyl methacrylate copolymers with a molar ratio of their respective monomers of 1:1 (Eudragit L®), methacrylic acid/methyl methacrylate copolymers with a molar ratio of the respective monomers of 1:2 (Eudragit S®), methacrylic acid/ethyl acrylate copolymers with a molar ratio of the respective monomers of 1:1 (Eudragit L30D-55®) methacrylic acid/methyl acrylate/methyl methacrylate copolymers with a molar ratio of the respective monomers of 7:3:1 (Eudragit FS®), shellac hydroxypropylmethylcellulose acetate succinates, cellulose acetate phthalates or a mixture of at least two of these components, which may also be employed where appropriate in combination with the aforementioned water-insoluble poly (meth)acrylates, preferably in combination with Eudragit NE30D® and/or Eudragit RL® and/or Eudragit RS®.

The release-slowing coatings and/or coatings which do not slow release can be applied by conventional methods suitable for the particular coating and known to the skilled worker, such as, for example, by spraying on solutions, dispersions or suspensions, by melting methods or by powder-application methods. The solutions, dispersions or suspensions can be employed in the form of aqueous or organic solutions of dispersions. Aqueous dispersions are preferably employed in this case. Organic solvents which can be used are alcohols, for example ethanol or isopropanol, ketones such as, for example, acetone, esters, for example ethyl acetate, chlorinated hydrocarbons such as, for example, dichloromethane, with alcohols and ketones preferably being employed. It is also possible to employ mixtures of at least two of the aforementioned solvents.

Where the medicament of the invention includes the racemate of tramadol in multiparticulate form, the release-slowing coating is preferably applied in such a way that the multiparticulate forms containing the racemic tramadol are coated after their production with the respective release-slowing polymers and, where appropriate, physiologically tolerated excipients from aqueous and/or organic media, preferably from aqueous media, with the aid of the fluidized bed method, and the coating is preferably dried and where appropriate, if necessary, heat-treated at the same time at conventional temperatures in the fluidized bed and/or a coating of (+)-tramadol is applied.

For poly(meth)acrylate coatings, the coating is preferably dried at an inlet air temperature in the range from 30 to 50° C., particularly preferably in the range from 35 to 45° C.

For cellulose-based coatings, such as, for example, ethylcellulose of cellulose acetate, the drying preferably takes place at a temperature in the range from 50 to 80° C., particularly preferably in the range from 55 to 65° C.

Wax coatings can be applied by melt coating in the fluidized bed and, after the coating, be cooled for complete solidification at temperatures below the particular melting range. Wax coatings can also be applied by spraying on solutions thereof in organic solvents.

To modify the active ingredient release profile, the medicament of the invention may also comprise the racemate of tramadol, preferably uniformly distributed, in a release-slowing matrix.

Matrix materials which can be used are physiologically tolerated, hydrophilic materials which are known to the skilled worker. Hydrophilic matrix materials preferably used are polymers, particularly preferably cellulose ethers, cellulose esters and/or acrylic resins. The matrix materials very particularly preferably employed are ethylcellulose, hydroxypropylmethylcellulose, hydroxypropylcellulose, hydroxymethylcellulose, poly-(meth)acrylic acid and/or derivatives thereof, such as the salts, amides or esters thereof.

Matrix materials composed of hydrophobic materials are likewise preferred, such as hydrophobic polymers, waxes, fats, long-chain fatty acids, fatty alcohols or corresponding esters or ethers or mixtures thereof. Hydrophobic materials particularly preferably employed are mono- or diglycerides of $C_{12}$-$C_{30}$ fatty acids and/or $C_{12}$-$C_{30}$ fatty alcohols and/or waxes or mixtures thereof.

It is also possible to employ mixtures of the aforementioned hydrophilic and hydrophobic materials as release-slowing matrix material.

The tramadol racemate which is present in the release-slowing matrix can be produced by conventional methods known to the skilled worker, and the formulation with (+)-tramadol to give the medicaments of the invention can take place as indicated previously.

The total amount of slow-release and immediate-release tramadol active ingredient to be administered to the patient varies for example depending on the patient's weight, on the indication and the severity of the pain or the disorder. The amount to be administered of the slow-release and immediate-release active ingredient, and the release thereof, is preferably adjusted so that administration of the medicament is necessary at most twice, preferably only once, a day and, at the same time, an adequate immediate effect occurs after administration.

The medicament of the invention is preferably suitable for controlling pain or for treating urinary incontinence, cough, depression, diarrhea or mental disorders. The medicament of the invention is particularly preferably employed for controlling acute or chronic pain.

The medicament of the invention has the advantage that it enables very severe pain to be satisfactorily controlled, while the frequency or the strength of the adverse drug reactions which occur where appropriate with tramadol, such as, for example, nausea, vomiting, sweating, dry mouth, dizziness, convulsions or drowsiness increases only slightly or not at all. Immediately after administration of the medicament to the patient, (+)-tramadol is available for metabolic activation by the enzyme CYP2D6 to the metabolite (+)—O-demethyltramadol, which has strong analgesic activity, so that the medicament of the invention is particularly suitable also for controlling very severe acute pain.

For controlling moderate or severe pain, the total dose of tramadol active ingredient to be administered to the patient can be reduced compared with conventional tramadol formulations which, besides slow-release tramadol racemate, also contain an initial dose of racemic tramadol, without the analgesic efficacy of tramadol being reduced thereby. This has the advantage that the adverse drug reactions which occur where appropriate with tramadol occur less often or in attenuated form.

A further advantage of the medicament of the invention is that the very low addictive and dependence potential of conventional tramadol formulations is retained, while the contribution of the opioid active component to controlling pain is increased.

The release of (+)- and (−)-tramadol from the medicament of the invention was determined as follows:

The particular formulation of the medicament of the invention was tested in the rotating basket apparatus or the paddle stirrer apparatus of Pharm. Eur. at a release medium temperature of 37±0.5° C. at a speed of rotation of 100 revolutions per minute in the case of the rotating basket apparatus and 75 revolutions per minute in the case of the paddle stirrer apparatus in 600 ml of simulated gastric fluid at pH 1.2 without enzymes for 2 hours. The formulation was then tested in 600 ml of simulated intestinal fluid at pH 7.2 without enzymes for a further 8 hours. The amount of (+)-tramadol and (−)-tramadol released at each time was determined by HPLC. The values presented are the averages from 6 samples in each case.

The invention is explained by means of examples below. These explanations are merely by way of example and do not restrict the general concept of the invention.

EXAMPLES

Example 1

Production of Pellets:

Pellets containing the racemate of tramadol with an active ingredient content of 55% by weight were produced by aqueous granulation with microcrystalline cellulose and low-substituted hydroxypropylcellulose and subsequent extrusion and spheronization. The pellets obtained in this way were dried, screened to a size of from 800-1 250 μm and then film-coated in a fluidized bed at an inlet air temperature of 60° C. firstly with 3% by weight hydroxypropylmethylcellulose and talc as coating and subsequently with 11% by weight Surelease® E-7-7050 as release-slowing coating. The film applications are in each case indicated in percent by weight based on the initial weight of the pellets or of the coated pellets.

Pellets containing the (+) enantiomer of tramadol with an active ingredient content of 55% by weight were produced by aqueous granulation with microcrystalline cellulose and low-substituted hydroxypropylcellulose and subsequent extrusion and spheronization. The pellets obtained in this way were dried and screened to a size of 800 to 1 250 μm. These pellets were then coated with a hydroxypropylmethylcellulose (Opadry OY 29020 clear®) coating which did not slow release.

Hard gelatin capsules of size 1 were then charged in a suitable two-piece capsule machine with 212 mg of slow-release pellets containing racemic tramadol (equivalent to 100 mg of racemic tramadol hydrochloride) and 47 mg of the immediate-release pellets containing the (+) enantiomer of tramadol (equivalent to 25 mg (+)-tramadol hydrochloride).

Composition per Capsule:

| | |
|---|---|
| Pellets containing tramadol racemate: | 212.0 mg |
| Racemic tramadol hydrochloride | 100.0 mg |
| Microcrystalline cellulose (Avicel PH 105 ® from FMC) | 42.7 mg |
| Low-substituted hydroxypropylcellulose (I-HPC LH 31 ® from ShinEtsu) | 40.8 mg |
| Hydroxypropylmethylcellulose Opadry OY 29020 clear ® (Colorcon) | 4.8 mg |
| Talc | 1.6 mg |
| Ethylcellulose | 22.1 mg |
| Surelease E-7-7050 ® (Colorcon) | |
| Pellets containing the (+) enantiomer of tramadol | 47.0 mg |
| (+)-Tramadol hydrochloride | 25.0 mg |
| Microcrystalline cellulose (Avicel PH 105 ® from FMC) | 10.5 mg |
| Low-substituted hydroxypropylcellulose (I-HPC LH 31 ® from ShinEtsu) | 10.0 mg |
| Hydroxypropylmethylcellulose Opadry OY 29020 clear ® (Colorcon) | 1.2 mg |
| Talc | 0.3 mg |

The release profile was determined in the rotating basket apparatus by the method indicated above and is shown in table 1 below.

TABLE 1

| Time in minutes | Amount of (+)-tramadol released in mg | Amount of (−)-tramadol released in mg |
|---|---|---|
| 30 | 25 | 0 |
| 120 | 28 | 4 |
| 240 | 40 | 15 |
| 360 | 55 | 31 |
| 480 | 65 | 41 |
| 600 | 74 | 49 |

Example 2

Pellets containing tramadol racemate and pellets containing the (+) enantiomer of tramadol of the compositions indicated below were produced and coated in analogy to example 1.

Hard gelatin capsules of size 0 were then charged in a suitable two-piece capsule machine with 212 mg of the slow-release pellets containing racemic tramadol (equivalent to 100 mg of racemic tramadol hydrochloride) and 94 mg of the immediate-release pellets containing the (+) enantiomer of tramadol (equivalent to 50 mg of (+)-tramadol hydrochloride).

Composition per Capsule:

| | |
|---|---|
| Pellets containing tramadol racemate: | 212.0 mg |
| Racemic tramadol hydrochloride | 100.0 mg |
| Microcrystalline cellulose (Avicel PH 105 ® from FMC) | 42.7 mg |
| Low-substituted hydroxypropylcellulose (l-HPC LH 31 ® from ShinEtsu) | 40.8 mg |
| Hydroxypropylmethylcellulose Opadry OY 29020 clear ® (Colorcon) | 4.8 mg |
| Talc | 1.6 mg |
| Ethylcellulose Surelease E-7-7050 ® (Colorcon) | 22.1 mg |
| Pellets containing the (+) enantiomer of tramadol | 94.0 mg |
| (+)-Tramadol hydrochloride | 50.0 mg |
| Microcrystalline cellulose (Avicel PH 105 ® from FMC) | 21.0 mg |
| Low-substituted hydroxypropylcellulose (l-HPC LH 31 ® from ShinEtsu) | 20.0 mg |
| Hydroxypropylmethylcellulose Opadry OY 29020 clear ® (Colorcon) | 2.4 mg |
| Talc | 0.6 mg |

The release profile was determined in the rotating basket apparatus by the method indicated above and is shown in table 2 below.

TABLE 2

| Time in minutes | Amount of (+)-tramadol released in mg | Amount of (−)-tramadol released in mg |
|---|---|---|
| 30 | 51 | 0 |
| 120 | 52 | 3 |
| 240 | 64 | 14 |
| 360 | 81 | 32 |
| 480 | 92 | 42 |
| 600 | 99 | 50 |

Example 3

Racemic tramadol hydrochloride was homogeneously mixed with microcrystalline cellulose, hydroxypropylmethylcellulose, colloidal silica and magnesium stearate in a cube mixer.

(+)-Tramadol chloride was homogeneously mixed with microcrystalline cellulose, colloidal silica and magnesium stearate in a cube mixer. The two mixtures were then compressed in a tablet press (Korsch EK0) eccentric to bilayer tablets with an average diameter of 12 mm. This was done by initially introducing 250 mg of powder mixture of the first layer into the die and precompressing by hand and, after addition of 100 mg of mixture of the second layer, finally compressing the tablets.

Composition of a bilayer tablet:

| | |
|---|---|
| 1st Layer | |
| Racemic tramadol hydrochloride | 100.0 mg |
| Microcrystalline cellulose (Avicel PH 101 ® from FMC) | 82.0 mg |
| Hydroxypropylmethylcellulose | 63.0 mg |
| type 2910, 100 000 mPas (Metolose 90 SH 100 000 ® ShinEtsu) | |
| Colloidal silica (Aerosil ®, Degussa) | 2.5 mg |
| Magnesium stearate | 2.5 mg |
| Total (1st layer) | 250 mg |
| 2nd Layer | |
| (+)-Tramadol hydrochloride | 50.0 mg |
| Microcrystalline cellulose (Avicel PH 101 ® from FMC) | 48.0 mg |
| Colloidal silica (Aerosil ®, Degussa) | 1.0 mg |
| Magnesium stearate | 1.0 mg |
| Total (2nd layer) | 100 mg |
| Total (bilayer tablet) | 350 mg |

The release profile was determined in the rotating basket apparatus by the method indicated above and is shown in table 3 below. In a deviation from the indicated method, testing in the simulated intestinal fluid was for 10 hours.

TABLE 3

| Time in minutes | Amount of (+)-tramadol released in mg | Amount of (−)-tramadol released in mg |
|---|---|---|
| 30 | 57 | 10 |
| 60 | 67 | 17 |
| 120 | 79 | 27 |
| 180 | 83 | 33 |
| 240 | 85 | 37 |
| 360 | 92 | 42 |
| 480 | 96 | 44 |
| 600 | 97 | 48 |
| 720 | 97 | 49 |

The invention claimed is:

1. A medicament comprising (a) the racemate of tramadol or a physiologically tolerated salt thereof in slow-release form and (b) the (+) enantiomer of tramadol or a physiologically tolerated salt thereof in immediate-release form.

2. The medicament as claimed in claim 1, wherein at least one of the racemate or (+) enantiomer is present in the form of a physiologically tolerated salt.

3. The medicament as claimed in claim 2, wherein the physiologically tolerated salt is selected from the group consisting of chloride, bromide, sulfate, sulfonate, phosphate, tartrate, teoclate, embonate, formate, acetate, propionate, benzoate, oxalate, succinate, citrate, diclofenacate, naproxenate, salicylate, acetyl-salicylate, glutamate, fumarate, aspartate, glutarate, stearate, butyrate, malonate, lactate, mesylate, saccharinate, cyclamate and acesulfamate.

4. The medicament as claimed in claim 1, which comprises from 10 to 75% by weight of (+)-tramadol and from 90 to 25% by weight of slow-release racemic tramadol, calculated as free active ingredient and based on the total amount of active ingredients.

5. The medicament as claimed in claim 1, which is in a form suitable for oral or parenteral administration.

6. The medicament as claimed in claim 1, which comprises the racemate and (+) enantiomer in separately formulated subunits.

7. The medicament as claimed in claim 6, wherein the subunits are different layers of a multilayer tablet.

8. The medicament as claimed in claim 6, wherein the subunits are present in multiparticulate form.

9. The medicament as claimed in claim 7, which comprises the racemate in slow-release subunits that are provided with a coating containing the (+) enantiomer.

10. The medicament as claimed in claim 1, wherein the slow release form comprises at least one of the racemate coated by a release-slowing coating, embedded in a release-slowing matrix, or attached to an ion-exchange resin.

11. The medicament as claimed in claim 10, which comprises a release-slowing coating based on one or more components selected from the group consisting of water-insoluble optionally modified natural or synthetic polymers and natural, semisynthetic or synthetic waxes or fats or fatty alcohols.

12. The medicament as claimed in claim 11, wherein the release-slowing coating is based on water-insoluble polymers, and the water-insoluble polymers are poly(meth)acrylates and/or copolymers thereof.

13. The medicament as claimed in claim 11, wherein the release-slowing coating is based on water-insoluble polymers, and the water-insoluble polymers are cellulose derivatives.

14. The medicament as claimed in claim 12, wherein the release-slowing coating is based on polymers that have been applied from aqueous medium.

15. The medicament as claimed in claim 11, wherein the release-slowing coating is based on a mixture of polyvinyl acetate and polyvinylpyrrolidone.

16. The medicament as claimed in claim 11, wherein the release-slowing coating is based on a wax, and the wax comprises one or more members selected from the group consisting of carnauba wax, beeswax, glycerol monostearate, glycerol monobehenate, glycerol ditripalmitostearate, and microcrystalline wax.

17. The medicament as claimed in claim 11, wherein the release-slowing coating comprises one or more polymers in combination with at least one plasticizer.

18. The medicament as claimed in claim 17, wherein the plasticizers are selected from the group consisting of lipophilic diesters of $C_{6-40}$ aliphatic or aromatic dicarboxylic acids and $C_{1-8}$ aliphatic alcohols, hydrophilic or lipophilic esters of citric acid, polyalkylene glycols, esters of glycerol, acetylated mono- and/or diglycerides, medium chain-length triglycerides, and oleic acid.

19. The medicament as claimed in claim 17, wherein the plasticizer is employed in an amount ranging from 5 to 50% by weight based on the weight of polymers in the release-slowing coating.

20. The medicament as claimed in claim 10, which comprises a release-slowing matrix based on a hydrophilic matrix material.

21. The medicament as claimed in claim 10, which comprises a release-slowing matrix based on a hydrophobic matrix material.

22. The medicament as claimed in claim 1, which comprises at least one protective coating.

23. The medicament as claimed in claim 22, wherein the protective coating improves the taste of the medicament.

24. The medicament as claimed in claim 22, wherein the protective coating is resistant to gastric fluid.

25. The medicament as claimed in claim 24, wherein the protective coating resistant to gastric fluid consists of one or more components selected from the group consisting of methacrylic acid/methyl methacrylate copolymers with a monomer molar ratio of 1:1, methacrylic acid/methyl methacrylate copolymers with a monomer molar ratio of 1:2, methacrylic acid/ethyl acrylate copolymers with a monomer molar ratio of 1:1, methacrylic acid/methyl acrylate/methyl methacrylate copolymers with a monomer molar ratio of 7:3:1, shellac, hydroxypropylmethylcellulose acetate succinate, and cellulose acetate phthalate, optionally in combination with poly(meth)acrylates.

26. A method of controlling pain comprising administering to a patient in need thereof an effective pain controlling amount of the medicament of claim 1.

27. The method of claim 26, where the pain is acute pain.

28. The method of claim 26, where the pain is chronic pain.

29. A method of treating urinary incontinence comprising administering to a patient in need thereof an effective amount therefor of the medicament of claim 1.

30. A method of treating cough comprising administering to a patient in need thereof an effective amount therefor of the medicament of claim 1.

31. A method of treating depression comprising administering to a patient in need thereof an effective amount therefor of the medicament of claim 1.

32. A method of treating diarrhea comprising administering to a patient in need thereof an effective amount therefor of the medicament of claim 1.

33. A method of treating mental disorders comprising administering to a patient in need thereof an effective amount therefor of the medicament of claim 1.

34. The medicament of claim 10, where the release-slowing coating is selected from water insoluble polymer, waxes or combinations thereof, where the water insoluble polymer is an ethyl acetate/methyl methacrylate copolymer with a monomer molar ratio of 2:1, and the wax is Carnuba wax.

35. The medicament of claim 34, where the water-insoluble polymer is plasticized by dibutyl sebacate plasticizer.

36. The medicament of claim 35, further comprising a non-slow release coating where the non-slow release coating is methacrylic acid/methyl methacrylate copolymer with a monomer molar ratio of 1:1.

37. The medicament of claim 3, where the physiologically tolerated salt is selected from the group consisting of chloride, sulfate, saccharinate, teoclate, embonate, diclofenacate, naproxenate and salicylate.

38. The medicament of claim 3, where the physiologically tolerated salt is chloride.

39. The medicament of claim 4, which comprises from 20 to 50% by weight of (+)-tramadol and from 80 to 50% by weight of slow-release racemic tramadol, calculated as free active ingredient and based on the total amount of active ingredients.

40. The medicament as claimed in claim 11, where the water-insoluble polymers are alkylcelluloses.

41. The medicament as claimed in claim 11, where the water-insoluble polymer is cellulose acetate.

42. The medicament as claimed in claim 17, where the plasticizer is present in amounts of from 10 to 30% by weight of the polymers in the release-slowing coating.

43. The medicament as claimed in claim 5, which is in a form suitable for oral administration.

44. The medicament as claimed in claim 7, wherein the subunits are different layers of a bilayer tablet.

45. The medicament as claimed in claim 8, wherein the subunits are present in a multiparticulate form selected from the group consisting of microtablets, microcapsules, granules, active ingredient crystals and pellets.

46. The medicament as claimed in claim 12, wherein the water-insoluble polymers are one or more members selected from the group consisting of poly($C_{1-4}$)-alkyl (meth)acrylates, poly($C_{1-4}$)dialkylamino-($C_{1-4}$)-alkyl (meth)acrylates and copolymers thereof.

47. The medicament as claimed in claim 46, wherein the water-insoluble polymers are one or more members selected from the group consisting of ethyl acrylate/methyl methacrylate copolymers with a monomer molar ratio of 2:1, and ethyl acrylate/methyl methacrylate/trimethylammoniumethyl methacrylate chloride copolymers with a monomer molar ratio of 1:2:0.1, ethyl acrylate/methyl methacrylate/trimethylammoniumethyl methacrylate chloride copolymers with a monomer molar ratio of 1:2:0.2.

48. The medicament as claimed in claim 14, wherein the polymers have been applied from aqueous latex or pseudolatex dispersions.

49. The medicament as claimed in claim 20, wherein the hydrophilic matrix material comprises one or more hydrophilic polymers.

50. The medicament as claimed in claim 49, wherein the one or more hydrophilic polymers are selected from the group consisting of cellulose ethers, cellulose esters and acrylic resins.

51. The medicament as claimed in claim 50, wherein the one or more hydrophilic polymers are selected from the group consisting of ethylcellulose, hydroxypropylmethylcellulose, hydroxypropylcellulose, hydoxymethylcellulose cellulose and poly(meth)acrylic acid and salts, amides and esters thereof.

52. The medicament as claimed in claim 21, wherein the hydrophobic matrix material comprises one or more members selected from the group consisting of hydrophobic polymers, waxes, fats, long-chain fatty acids, fatty alcohols and esters, ethers and mixtures thereof.

53. The medicament as claimed in claim 52, wherein the hydrophobic matrix material comprises one or more members selected from the group consisting of mono- or diglycerides of $C_{12}$-$C_{30}$ fatty acids, $C_{12}$-$C_{30}$ fatty alcohols and waxes.

* * * * *